(12) United States Patent
Ehrhardt

(10) Patent No.: US 11,513,057 B2
(45) Date of Patent: Nov. 29, 2022

(54) SYSTEMS AND METHOD FOR RAPID IDENTIFICATION AND ANALYSIS OF CELLS IN FORENSIC SAMPLES

(71) Applicant: VIRGINIA COMMONWEALTH UNIVERSITY, Richmond, VA (US)

(72) Inventor: Christopher Ehrhardt, Midlothian, VA (US)

(73) Assignee: Virginia Commonwealth University, Richmond, VA (US)

(*) Notice: Subject to any disclaimer, the term of this patent is extended or adjusted under 35 U.S.C. 154(b) by 217 days.

(21) Appl. No.: 16/959,191

(22) PCT Filed: Jan. 4, 2019

(86) PCT No.: PCT/US2019/012329
§ 371 (c)(1),
(2) Date: Jun. 30, 2020

(87) PCT Pub. No.: WO2019/136234
PCT Pub. Date: Jul. 11, 2019

(65) Prior Publication Data
US 2020/0400548 A1  Dec. 24, 2020

Related U.S. Application Data

(60) Provisional application No. 62/613,657, filed on Jan. 4, 2018.

(51) Int. Cl.
| | |
|---|---|
| *G01N 15/14* | (2006.01) |
| *G16H 10/40* | (2018.01) |
| *G16H 30/40* | (2018.01) |
| *G01N 15/10* | (2006.01) |

(52) U.S. Cl.
CPC ......... *G01N 15/1456* (2013.01); *G16H 10/40* (2018.01); *G16H 30/40* (2018.01); *G01N 2015/1006* (2013.01); *G01N 2015/1477* (2013.01); *G01N 2015/1488* (2013.01)

(58) Field of Classification Search
CPC ....... G01N 15/1456; G01N 2015/1006; G01N 2015/1477; G01N 2015/1488; G16H 10/40; G16H 30/40
See application file for complete search history.

(56) References Cited

U.S. PATENT DOCUMENTS

| | | |
|---|---|---|
| 8,067,170 B2 | 11/2011 | Chakrabarty |
| 10,989,724 B1* | 4/2021 | Holmes ................. G01N 35/02 |
| 2005/0233318 A1 | 10/2005 | Chee et al. |
| 2013/0078624 A1* | 3/2013 | Holmes ..................... C12Q 1/00 73/61.52 |

FOREIGN PATENT DOCUMENTS

| | | |
|---|---|---|
| WO | 2012/178166 A1 | 12/2012 |
| WO | 2015/008245 A2 | 1/2015 |

* cited by examiner

*Primary Examiner* — David P Porta
*Assistant Examiner* — Fani Polyzos Boosalis
(74) *Attorney, Agent, or Firm* — WCF IP

(57) ABSTRACT

High-throughput methods and systems for using morphological and/or autofluorescence signatures of cells to characterize unknown cell/tissue types within a forensic sample are provided. Machine learning algorithms are used to correlate morphological and/or autofluorescence signatures to characteristics such as cell type.

26 Claims, 9 Drawing Sheets

SYSTEMS AND METHOD FOR RAPID IDENTIFICATION AND ANALYSIS OF CELLS IN FORENSIC SAMPLES

FIELD OF THE INVENTION

The invention is generally related to systems and methods which enable rapid identification and analysis of cells in forensic samples. More particularly, aspects of the invention utilize autofluorescence and/or morphological signatures of cells to determine characteristics of the forensic sample such as the contributor(s), cell type, and quantity within the sample.

BACKGROUND

Characterizing cells present in biological evidence, such as determining the tissue they originated from within the body, can assist with crime reconstructions and downstream DNA profiling methods. Traditionally, caseworking methods for determining tissue source are based on microchemical and/or enzymatic reactions targeted toward proteins within bodily fluids, which have limited sensitivity and/or specificity. Recently, there has been considerable research into biomolecular markers for tissue identification. These include mRNA transcripts [1], micro-RNAs [2,3], proteomics [4], and DNA methylation patterns [5]. Although promising, the specificity of many of these systems is still being investigated and interpretation can require complex bioinformatic workflows. In particular, microchemical reactions are prone to false positive and false negative results and often have large sample requirements. Genetic tests (based on mRNA or microRNA profiles) can also be prone to false positive/negative results, consumes some amount of sample, and have not been fully validated for forensic casework.

No known forensic techniques have successfully utilized morphological or intrinsic biochemical differences to differentiate between cells from different tissues in samples approximating those encountered in forensic casework. This is likely due to the laborious nature of microscopic characterizations and the need for tissue-specific antibody probes which have limited success on dried or compromised samples [6,7]. Thus, there is a need in the art for systems and methods that are able to rapidly and accurately identify and characterize cells in forensic samples that overcome the shortcomings of the prior art.

SUMMARY

The present disclosure provides systems and methods that utilize the intrinsic properties of cells for analysis and characterization of forensic samples. The methods are non-destructive in that no biochemical or immunological stains or probes are required. In some aspects, high-throughput, single cell measurements may be combined with a multi-variate classification framework to extract autofluorescent and/or morphological signatures from biological samples to characterize and distinguish various cell types within a biological sample.

According to an aspect of some embodiments, a method of characterizing cells from an unknown contributor or contributors in a forensic sample comprises obtaining a plurality of morphological and/or autofluorescence measurements from a plurality of cells in the forensic sample; and classifying the plurality of cells into three or more groups using two or more binary classifications.

According to an aspect of some embodiments, a binary classification comprises calculating at least two coordinate values for each cell using respective first and second functions that are weighted combinations of the plurality of morphological and/or autofluorescence measurements, comparing the at least two coordinate values calculated for each cell against a distribution of coordinate values in a reference dataset, and sorting each cell into either a first group or a second group based on the comparison, wherein the three or more groups includes the first group and/or second group.

According to an aspect of some embodiments, two or more binary classifications are performed successively, wherein for any two binary classifications in immediate succession, only the cells sorted into the second group by the first binary classification are subjected to the second binary classification.

According to an aspect of some embodiments, the respective functions of the two or more binary classifications contain the same plurality of morphological and/or autofluorescence variables but different weightings.

According to an aspect of some embodiments, the comparison step comprises comparing ratios of multivariate distances between the calculated coordinate values and multivariate centroids of cell groups in the reference dataset.

According to an aspect of some embodiments, the three or more groups into which cells are classified are all epithelial cell types. In some embodiments the three or more classification groups comprise epidermal, buccal, and vaginal.

According to an aspect of some embodiments, the two or more binary classifications include a first binary classification that differentiates epidermal cells from non-epidermal cells and a second binary classification that differentiates buccal cells from vaginal cells, wherein the second binary classification is performed only for cells classified by the first binary classification as non-epidermal cells.

According to an aspect of some embodiments, a method comprises counting a total cell count for each of the final classification groups after all binary classifications are complete.

According to an aspect of some embodiments, the step of obtaining may comprise generating images of individual cells and analyzing the images to obtain the plurality of morphological and/or autofluorescence measurements. In some embodiments the measurements are obtained with an imaging flow cytometer.

According to an aspect of some embodiments, the one or more morphological and/or autofluorescence measurements are selected from the group consisting of area, aspect ratio, aspect ratio intensity, contrast, intensity, mean pixel, median pixel, max pixel, length, width, height, brightness detail intensity ('R3' pixel increment), raw centroid X, raw centroid Y, and circularity. The one or more known characteristics may be selected from the group consisting of cell type; time since cell deposition; and age, sex, and ethnicity of cell contributor.

According to an aspect of some embodiments, a method of training a computer for analysis of forensic samples comprises obtaining for a plurality of morphological and/or autofluorescence variables a plurality of measurements from a plurality of cells having one or more known characteristics; and generating two or more functions which are weighted combinations of the plurality of morphological and/or autofluorescence variables such that the variation between user-defined sample groups is maximized and within group variation is minimized.

DETAILED DESCRIPTION

Cells obtained from different subjects and different tissues or cells subject to different environmental conditions may have intrinsic biochemical, structural, and morphological variances. Embodiments of the disclosure provide high-throughput, non-destructive methods that use these variances to identify cell types, determine the age of an evidence stain, and infer phenotypic attributes of contributors in forensic biological samples. For example, some embodiments are especially well-suited for identification of epithelial cell types. Since the intrinsic properties of cells are being analyzed, no biochemical or immunological stains or probes are required. As discussed in the Example, multivariable classification frameworks may be used to distinguish and characterize unknown cell populations of a forensic sample with an overall high degree of accuracy.

Figure 1:
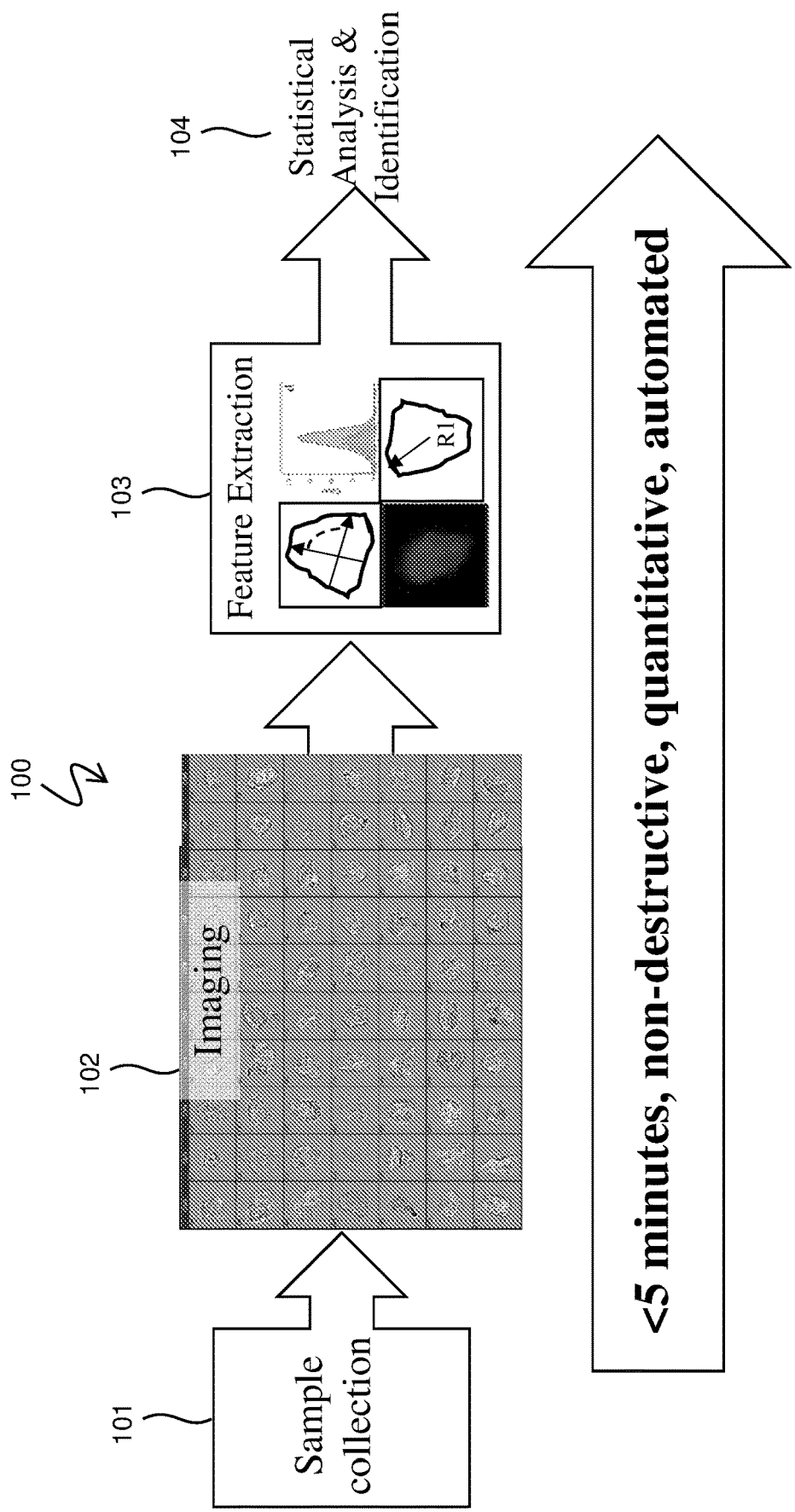
FIG. 1. Diagram of a rapid forensic cell testing process according to example embodiments of the disclosure.

FIG. 1 is a diagram of a process 100 for rapid forensic cell testing and analysis according to some exemplary embodiments. At a high level, the process includes sample collection 101, imaging 102, feature extraction 103, and statistical analysis and identification 104. Sample collection 101 refers to the obtaining physical cells, e.g., from a crime scene or rape victim. Imaging 102 comprises obtaining images (e.g., image data) of individual cells. Feature extraction 103 comprises obtaining measurements for a plurality of morphological and/or autofluorescence variables. Statistical analysis and identification 104 comprises employing the extracted features to make conclusions and inferences about the sampled cells. Block 104 may comprise cell type identification and cell quantification with respect to each cell type, for example. The use of high-throughput technology allows for rapid (e.g. less than 5 minutes), non-destructive, and quantitative sample analysis.

Many if not all of the features may be obtained from the images of block 102 and are thus non-destructive with respect to the original samples from block 101. This contrasts with certain analyses such as DNA analysis which use and destruction of the original cells. Absent context which indicates otherwise, this disclosure generally refers to cells and cell images interchangeably, with an understanding that the measurements are generally obtainable and indeed obtained from images of the cells, but the measurements ultimately characterize properties of the actual cells. A significant exception to this generalization is that some measurements are inextricably linked to both the original cell and the imaging technique. For example, a particular wavelength may be used to take a measurement, and a different wavelength may result in a different outcome. In such cases those of ordinary skill in the art will recognize that both the original cell being characterized and the imaging technique are underlying elements of the measurement or variable.

The fluorescent or morphological properties of cells may be identified and measured using any microscopy method known in the art, including field-portable technology. Typically, microscopes compatible with the methods of the disclosure include a camera for capturing images of cells and a processor for determining and analyzing fluorescent or morphological properties. In some embodiments, commercial or open source software platforms (e.g., [21]) are utilized.

Figure 2:
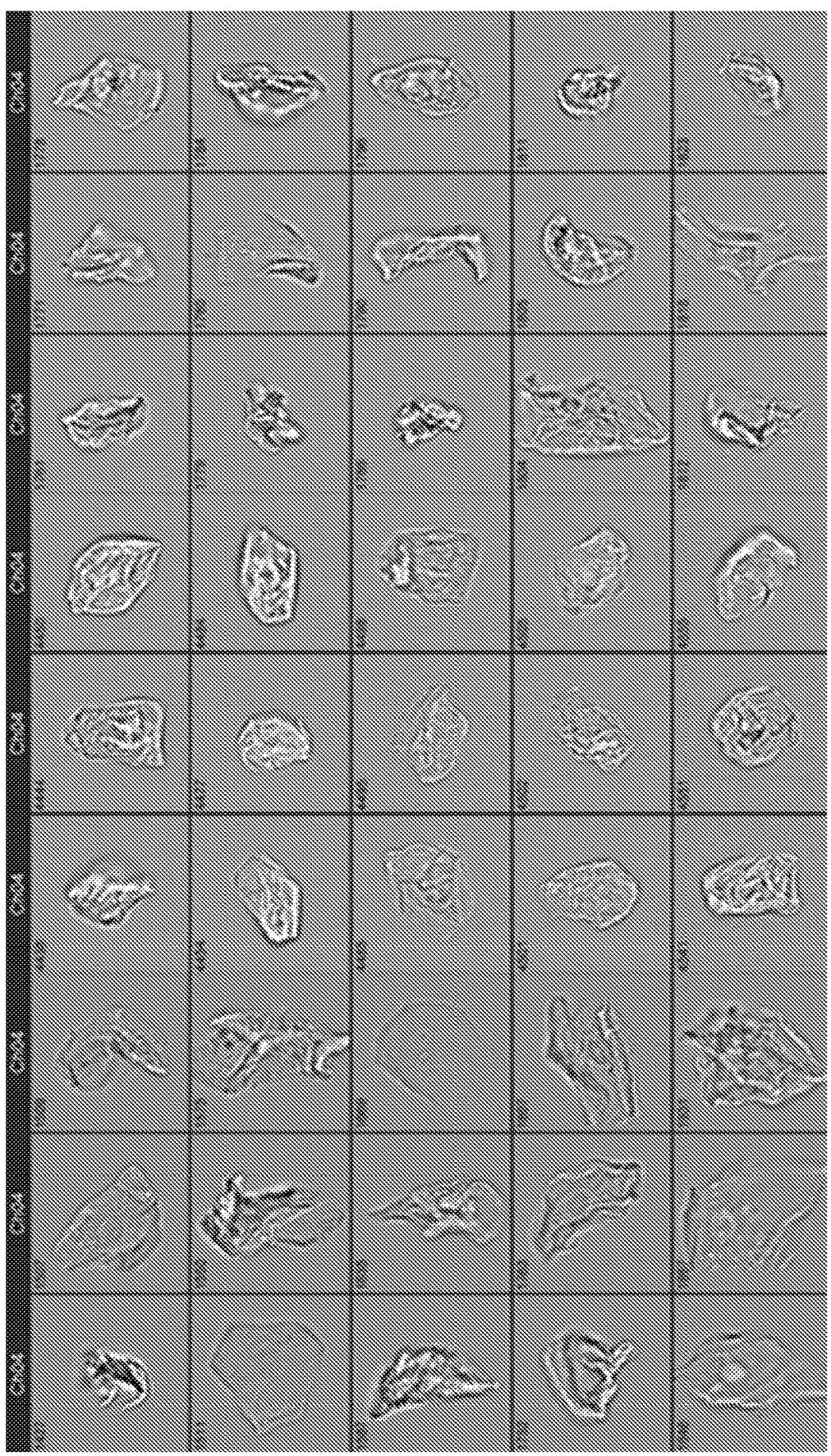
FIG. 2. Image gallery for three epithelial cell tissue sources. IFC brightfield images for buccal cells (columns 1-3), epidermal cells (columns 4-6), and vaginal cells (columns 7-9). Each image frame is 50 µm×50 µm. Object identifiers are included with each image.

FIG. 2 shows actual cell images according to known photographic methods for imaging cells at the time of the invention. Imaging techniques and technologies already in existence, presently under development, or not yet developed may be employed in different embodiments consistent with the disclosure herein. In other words, embodiments of the invention are not limited by the current state of the art of cell imaging technology, absent an express recitation in claims otherwise. The illustrative images of FIG. 2 are of actual individual cells imaged by a microscope. In some embodiments, the microscope is an imaging flow cytometer (IFC) which combines conventional flow cytometry analysis whereby the optical properties of individual cells are interrogated with lasers at set wavelengths (e.g. wavelengths from 300-750 nm) with fluorescence and bright field imaging of those same cells. IFC is routinely used in biomedical and clinical research for identification of unusual cell types as well as high resolution surveys of both cellular and sub-cellular processes [8]. The primary advantage of IFC over conventional microscopic analysis is that images of single cells are collected in a high throughput manner (as many as hundreds per second) and at multiple fluorescence channels simultaneously. The resulting multivariate data streams can therefore be used to compare profiles between individual cells or between larger populations. An exemplary commercially available IFC is the Amnis® Imagestream X Mark II imaging flow cytometer (EMD Millipore; Burlington, Mass.) equipped with 405 nm, 488 nm, 561 nm, and 642 nm lasers.

In some embodiments, data obtained from individual cells include features selected from, but not limited to, area, aspect ratio, aspect ratio intensity, contrast, intensity, mean pixel, median pixel, max pixel, length, width, height, brightness detail intensity ('R3' pixel increment), raw centroid X, raw centroid Y, and circularity. In some embodiments, a plurality (i.e. two or more) of these variables and/or additional variables and/or alternative variables may be used. (e.g., Brightness detail intensity in R7 pixel increment, elongatedness, compactness). In some embodiments, Fluorescence Intensity, Brightness Detail Intensity, Max Pixel Intensity, and Circularity appear particularly influential in classifying a cell correctly. In some embodiments, one or more of the aforementioned feature measurements are used for training a series of algorithms as described herein or for characterizing an unknown sample. These feature measurements may be collected across multiple, e.g. 2, 3, 4, 5, 6, or more, detector channels (e.g., fluorescence and brightfield wavelengths). Some measurements, such as centroid X/Y and circularity, may be determined using only brightfield images.

Figure 3:
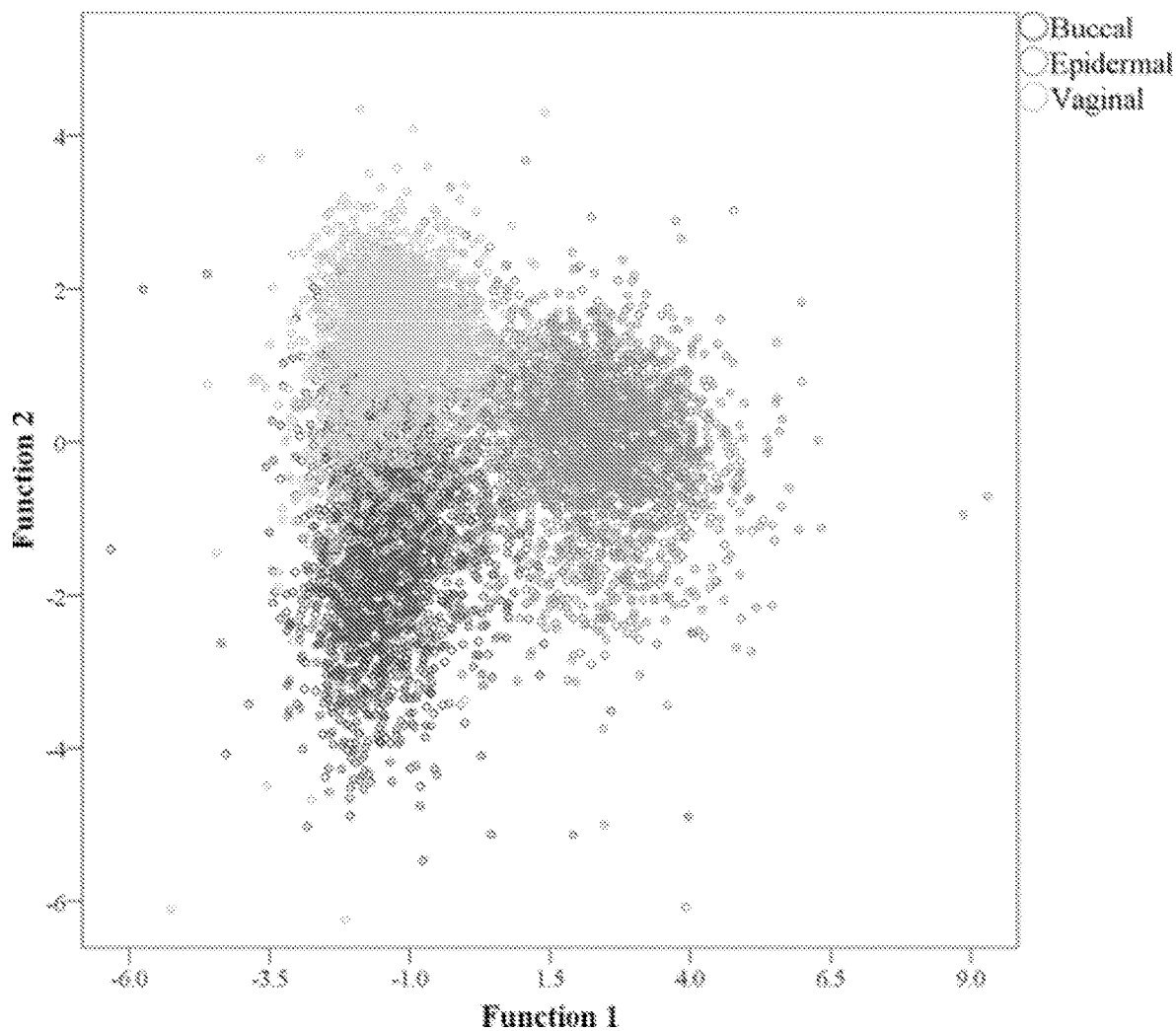
FIG. 3. Discriminant Function Analysis (DFA) of epithelial cells from three tissue sources using IFC variables. The first discriminant function (x-axis) accounted for ~74% of the between group variation and the second discriminant function (y-axis) accounted for ~26%.

FIG. 3 shows an exemplary type of graphical depiction available as an output to the process 100 of FIG. 1. Embodiments of the disclosure use imaging techniques to determine the autofluorescence and/or morphological signatures of cells in a sample. The extracted features are used to identify, for example, cell type and cell number. In FIG. 3, each point represents a single cell/image of a cell. The x- and y-axes are different functions which each yield a single numerical value for characterizing a given cell based on the extracted features. These functions are configured so that cells of the same type cluster when plotted, and cells of different types do not cluster when plotted. In some embodiments, the signatures allow for distinguishing between different types of epithelial cell types. FIG. 3 clearly shows the separation of three different cell types, namely buccal, epidermal, and vaginal. The generation of the functions for the axes of the plot in FIG. 3 is discussed in greater detail below in connection with FIGS. 6, 7A, and 7B. The use of high-throughput technology allows for rapid (e.g. less than 5 minutes), non-destructive, and quantitative sample analysis.

FIGS. 4A, 4B, 5A, and 5B are additional plots of cells in which the sampled cells and/or functions used for the axes have been modified. As with the plot in FIG. 3, cells sharing a certain common characteristic (e.g., cell type) are clustered together, whereas cells having certain different characteristics are more distant and belong to different clusters. These figures will be discussed in greater detail in the Example below.

Cell types that may be identified using methods of the disclosure include, but are not limited to buccal cells, vaginal cells, epidermal, and other skin or epithelial cells, and blood cells. The cells may be obtained from a forensic sample, such as a "touch" or "contact" sample left when a person touches a surface. Other sample types from which cells may be obtained include, but are not limited to, blood, urine, vaginal, semen, saliva, and hair samples. The methods of the present disclosure allow for the analysis of cells in such samples even when genetic material is not recoverable.

Figure 6:
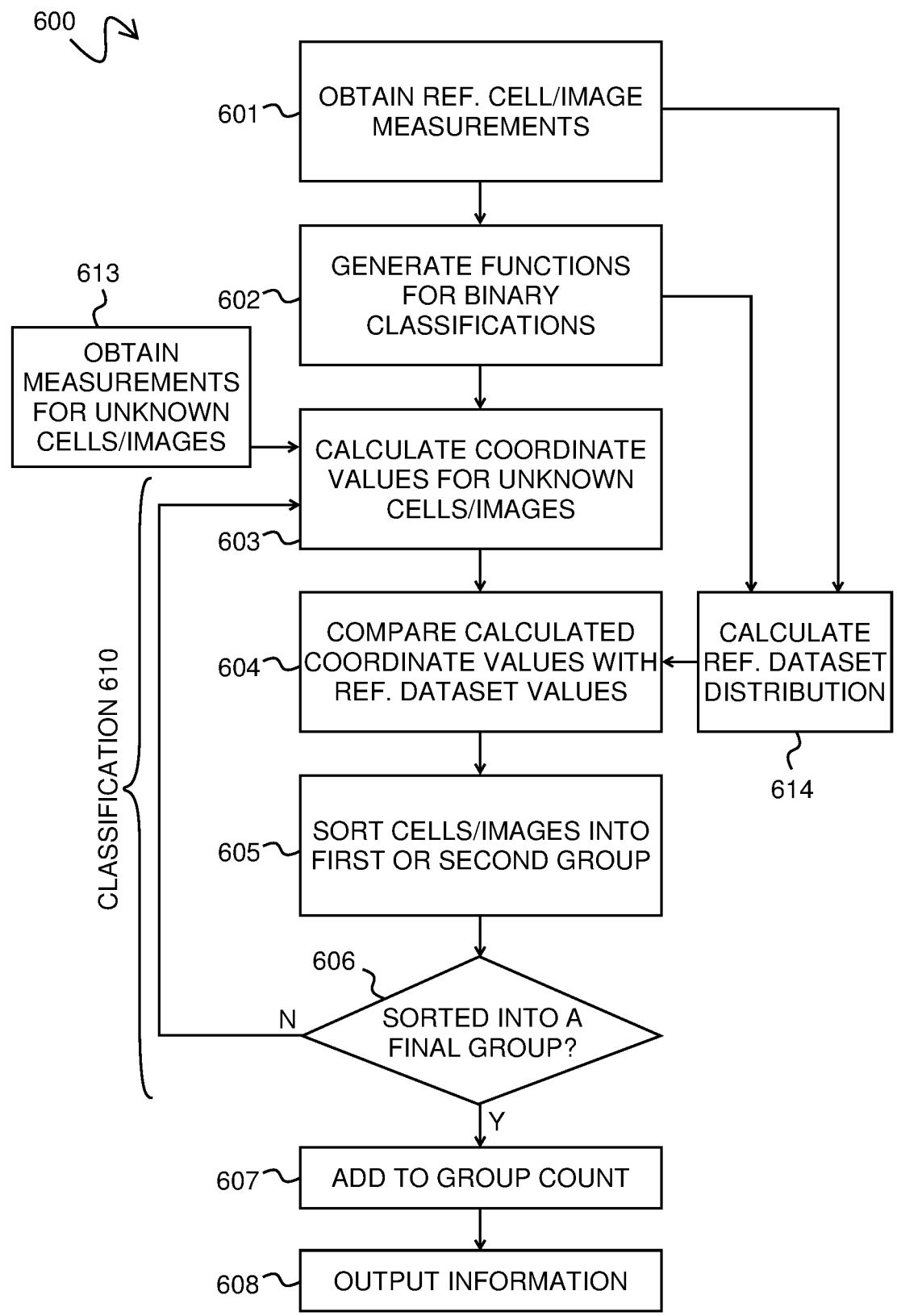
FIG. 6. Flow diagram of exemplary method for characterizing a plurality of cells, in particular classifying a population of cells by cell/tissue type.
Figure 7A:
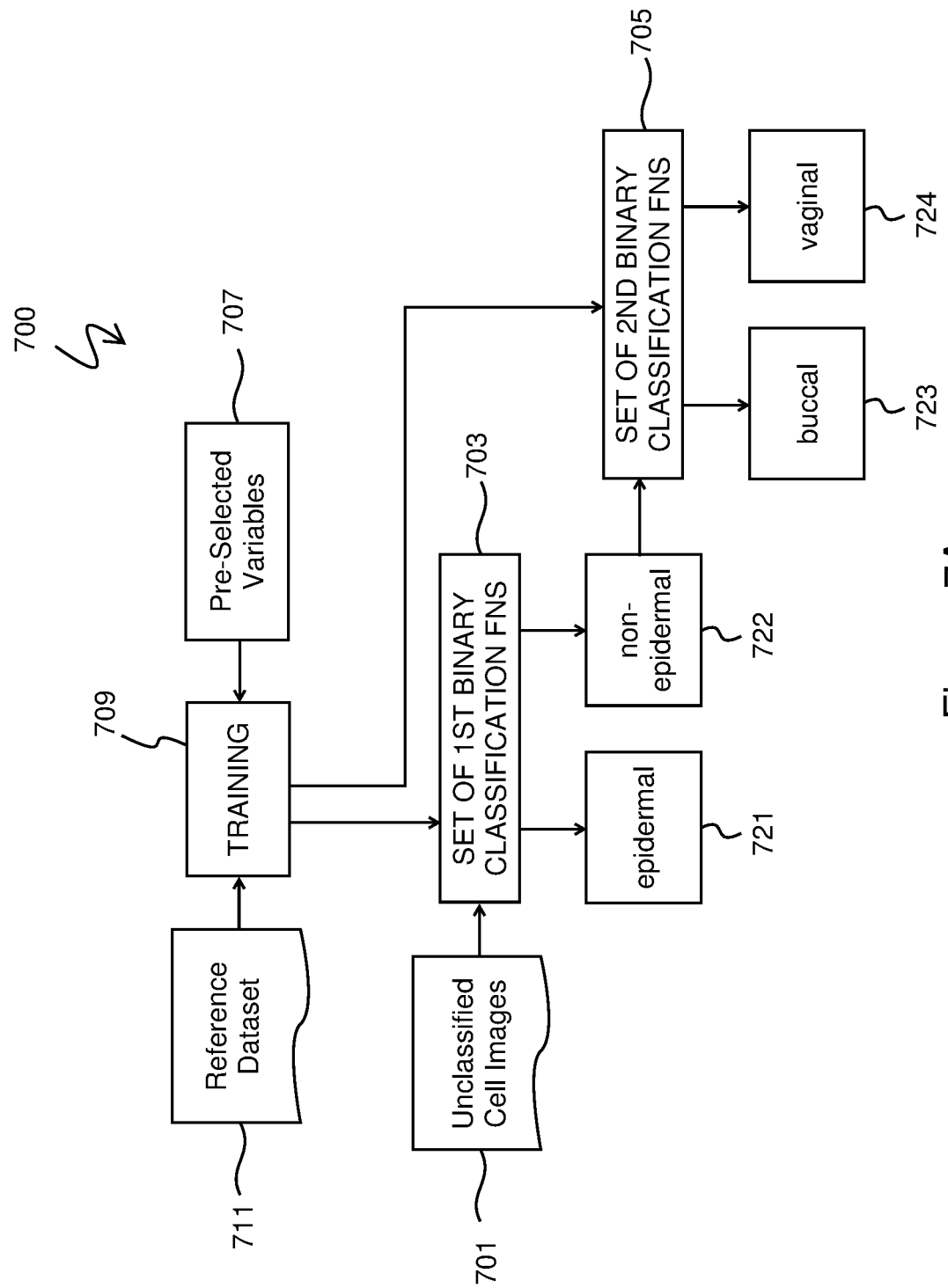
FIG. 7A. Block diagram of process for discriminating/classifying images of cells into a three different tissue/cell types.
Figure 7B:
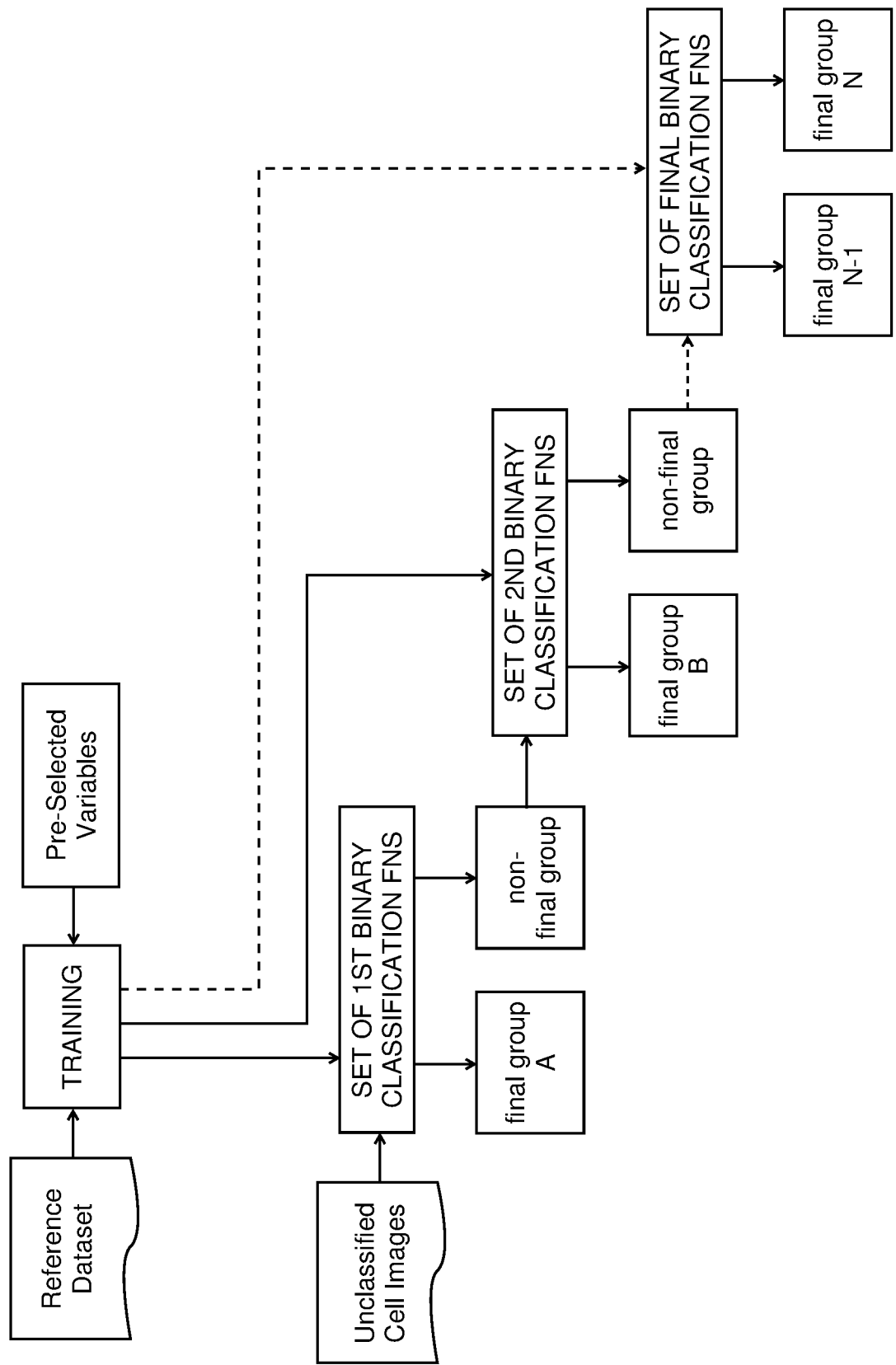
FIG. 7B. Block diagram of process for classifying images of cells into any number of different tissue/cell types.

FIG. 6 is a flowchart for an exemplary method 600 for characterizing a plurality of cells from an unknown contributor or contributors in a forensic sample. Contributors may be persons or parts thereof, such as organs (e.g., skin, vagina, anus, etc.). Generally, the method 600 may be used for classifying the plurality of cells into three or more groups using two or more binary classifications 610 which may be tiered or performed successively. FIGS. 7A and 7B, discussed below, provide further illustration of the tiered/successive implementation.

At block 601 reference measurements are obtained as a basis for the classification 610. The reference measurements are of a population or populations of cells of known type(s). At block 602 the reference measurements are used to generate functions for binary classification. At block 614 the reference measurements may then be inserted into the functions to produce a reference dataset containing a distribution of coordinate values. With blocks 601, 602, and 614 completed, a classification 610 may proceed.

Measurements for cells of unknown origin or contributor are obtained at block 613 and serve as the base input for a classification 610. A cell's image may be analyzed, and measurement data extracted, to determine values for variables such as area of cell, average pixel density, contrast, and aspect ratio, among others.

Generally, a single binary classification 610 comprises i) at block 603, calculating at least two coordinate values for each respective cell of unknown origin using the measurements of block 613 inserted into respective first and second functions of block 602, ii) at block 604, comparing the at least two coordinate values calculated for each cell against the reference dataset distribution of block 614, and iii) at block 605, sorting each cell into either a first group or a second group based on the comparison of block 604.

The comparison step at block 604 may comprise comparing ratios of multivariate distances between the calculated coordinate values and multivariate centroids of cell groups in the reference dataset. Cells which are being sorted may be plotted on the same plots as reference dataset cell populations. A reference dataset cell population may form a data point cluster which is characterized or characterizable with a centroid. A distance from the point of a cell being sorted to a reference dataset centroid may be determined. The distance may be multivariate (e.g., determined based on multiple cell characteristics using multiple classification functions). A determination may be made of whether the distance exceeds or does not exceed a predetermined threshold. Whether the threshold is or is not exceeded may be used to determine whether the cell being sorted is or is not related to the known cells of the reference dataset cluster/centroid. Comparisons of distances and/or thresholds may be expressed as ratios, e.g., ratios of multivariate distances between calculated coordinate values for cells being sorted and multivariate centroids of cell groups in a reference dataset. The sorting step at block 605 may include both a group classification for a given cell plus a probability estimate for the accuracy of that classification.

Some cells may require only one binary classification 610, while others may require two, three, four, or more successive classifications. Each binary classification 610 sorts a cell into one of two groups. In an exemplary method 600, the first group is a final group meaning sorting is complete for cells in that group. The second group may also be a final group, or the second group may require further processing by reprocessing with blocks 603, 604, and 605, this time with a different set of functions produced by block 602. For every final group, a total cell count/abundance may be calculated at block 607. Once the input cells (cell images) have been sorted into final groups, information is output at block 608. Block 608 may also be a continuous output process that updates output information as the process 600 is underway.

The output information of block 608 pertains to the three or more groups and is based on the classification 610. For example, the output information may include what final groups were used to classify, how many cells were sorted into each final group, what percentage of the cells from the input population of cells were sorted into each final group, classification accuracy probabilities for respective cells or groups of cells, and/or other information. The information output at block 608 may be output to a downstream computer/computer system/user, such as personnel or systems that use the information for downstream DNA profiling and/or crime reconstruction. The information output at block 608 may be output to a human user or a machine user, for example. Outputting may comprise or consist of printing, displaying on a screen or other display device, supplying an audio output, an electronic data transfer (wired or wireless), or some other means of output. Output information may be or include plots of the calculated coordinates with or without plotted points of the reference dataset. Such plots may be printed or displayed, for example.

FIG. 7A presents a process 700 for discriminating/classifying images of individual cells into a plurality of tissue/cell type categories/classifications/groups. The process 700 corresponds with the method 600 of FIG. 6 but uses specific cell types for illustrative purposes. The process 700 addresses the need to classify cells, or images 701 thereof, into a plurality of distinct groups, in particular exactly three final groups: epidermal, buccal, and vaginal. At the outset a population of cells or collection of cell images 701 are available, but the specific tissue or cell type characterizing each individual cell or image is unknown. For instance, the plurality of cells 701 may in fact be all buccal, all vaginal, all epidermal, a combination of buccal and vaginal, a combination of vaginal and epidermal, a combination of buccal and epidermal, or a combination of all three types.

The images 701, in particular measurements obtained therefrom (block 601 of FIG. 6) are used to calculate coordinate values for a set of functions of a first binary classification 703 (block 603 of FIG. 6). The calculated values, after a comparison with a reference dataset distribution (block 604 of FIG. 6), are sorted into a (final) epidermal group 721 or into a (non-final) non-epidermal group 722. Only the cells sorted into the non-epidermal group 722 are subjected to the successive or subsequent tier of binary classification functions 705. The second binary classification sorts all input cells into either the (final) buccal group 723 or (final) vaginal group 724.

The sets of classification functions 703 and 705 are weighted combinations of the plurality of morphological and/or autofluorescence variables 707. These variables may be pre-selected, e.g., by a human user, program, or device. The available variables are extensive and are discussed elsewhere in this disclosure. The weighted combinations may be linear sums. Accordingly a single classification function requires both a plurality of variables and a plurality of weights (generally, a single weight for each respective variable).

Weights may also be referred to as coefficients. For any given set of classification functions 703 or 705, the weights may be determined using one or more machine learning techniques (i.e., training 709) and a reference dataset 711. (Note that block 601 of FIG. 6 generally corresponds with block 701 of FIG. 7. Block 602 of FIG. 6 generally corresponds with both blocks 703 and 705 of FIG. 7.)

Training 709 (e.g., function generation block 602 of FIG. 6) determines weights using one or more of linear discriminant analysis, one or more artificial neural networks, and hierarchical clustering. For some embodiments a preferred means of generating classification functions is using a discriminant function analysis statistical approach whereby multivariate differences between cell type groups are maximized and multivariate differences within groups are minimized.

Generally, more variables 707 yield more accurate function sets 703 and 705. However, a minimum group of variables may be used to achieve an adequate result without undue processing burden. The minimum variable set, according to some exemplary embodiments, consists of Fluorescence Intensity, Brightness Detail Intensity, Max Pixel Intensity, and Circularity. Generally, however, a variable set will include these variables among others. In some instances the training 709 may give one or more variables a weight of close to zero or zero (e.g., −0.01 to 0.01, −0.001 to 0.001, 0). In some instances the training 709 gives every variable which is provided as an input a non-zero weight, either positive or negative.

Using a reference dataset and a training methodology such as discriminant function analysis as discussed above, classification functions are generated which may have appear as follows:

Coordinate #1=(−0.2*Area of cell in fluorescence channel 1)+(−0.1*Area of cell in brightfield channel)+(0.6*Aspect ratio in brightfield channel)+(0.1*Intensity of fluorescence in Channel 2)+(0.3*Intensity fluorescence in Channel 3)+(−0.2*Circularity of cell)+ . . .

Coordinate #2=(−0.7*Area of cell in fluorescence channel 1)+(−0.07*Area of cell in brightfield channel)+(0.2*Aspect ratio in brightfield channel)+(0.04*Intensity of fluorescence in Channel 2)+(0.1*Intensity fluorescence in Channel 3)+(−0.6*Circularity of cell)+ . . .

Of course the variables used in the equations depends on the variables 707 which are pre-selected, and the weight associated with each respective variable depends on the reference dataset employed in a given embodiment. As discussed above, the reference dataset is a population of cells or collection of cell images for which the cell or tissue type of each cell or cell image is already known. For example, the reference dataset may contain a collection of epithelial cell images which are each respectively known to be either buccal, vaginal, or epidermal. A single reference dataset may be used for a variety of cell images to be classified. Alternatively, different embodiments may employ different reference datasets.

Though the above description of FIGS. 6 and 7A has been described using buccal, vaginal, and epidermal as the candidate cell types for which cells may be classified, the algorithm may be adapted or modified based on the teachings herein for applicability to additional or alternative cell types.

FIG. 7B adapts process 700 for any number N of classification groups, where N may be 2, 3, 4, 5, 6, 7, 8, 9, 10, or more. The total number of sets of binary classification functions will then be N−1. Each binary classification yields one final group of sorted cells and a non-final group, with the exception of the final binary classification which yields two final groups.

Different combinations of cellular measurements may maximize classification accuracy particularly for cell types with similar biochemical and physical properties but different source tissue. For example, differences in red autofluorescence emissions (e.g. 650-670 nm) may be used to first identify and separate cells deposited by different contributors. Once separated, one or more morphological features may then be analyzed to determine, e.g. the cell type. In an exemplary embodiment, one or more of the size, circularity, intensity, and brightness detail of the cells may be used to distinguish between buccal, vaginal, and epidermal cells (see Example). In some embodiments, the overall size of the cells are used to distinguish between male and female contributors and/or between younger and older contributors. For example, female contributors generally have larger cells than male contributors and older contributors generally have larger cells than younger contributors.

Since most microscopic imaging methods (including IFC) are inherently non-destructive techniques, some embodiments of the disclosure allow for collecting and non-destructively classifying cells according to cell type before analysis for DNA profiling or other biological characterizations which may destroy the cells. Standard DNA profiling techniques may be used in conjunction with or supplemental to the methods disclosed herein, e.g. to increase the probative value of evidence and/or increase sample processing efficiency by identifying samples likely to provide greater DNA yield. This is due to the fact that intracellular DNA content characteristically varies across many tissue types (e.g., between differentiated epidermal cells and buccal cells); therefore identifying cell types and quantifying their abundance can often predict the DNA yield and the quality of the DNA profile likely to be produced from the sample. In some forensic sample types, the number of cells present will be proportional to the amount of DNA recovered. Additionally, some cell types have characteristically higher levels of intracellular DNA than others. For example, intact buccal and vaginal cells (that are nucleated) will have much more DNA in them than an epidermal cell. So detecting the presence of high levels of buccal cells in one sample over another can indicate that the sample will provide more DNA. In some embodiments, the flow cytometer is configured and used to determine the quantity or relative abundance of cells in a sample.

Identifying the presence of one or more of cell types in a biological sample when combined with DNA profiling results may be useful when evaluating either single source or mixture samples to explain the presence (or absence) of particular individuals' DNA (e.g., claims of sexual assault versus denial of such activity and suggestions of indirect transfer). Additionally, because DNA yield has been observed to systematically vary between epidermal cells and other types of epithelial tissue [9], determining the presence and relative quantities of each cell type can help direct downstream DNA profiling efforts.

During forensic casework, samples are often collected at different lengths of time after deposition and/or stored for different lengths of time prior to analysis. Some methods of the present disclosure allow for determining cell type (e.g., epithelial cell type) for cells of various ages, e.g., hours (e.g. 1-24 or more hours), days (e.g. 1-7 or more days), weeks (e.g. 1-5 or more weeks), months (e.g. 1-12 or more months), or years (e.g. 1-10 or more years).

Some embodiments may include algorithms configured for determining the "age" of a forensic sample, e.g. the time since a touch sample was deposited. As shown in the Example, fluorescent and/or morphological features of cells may change in a characteristic way over time. Depending on time from deposition to collection, and from collection to analysis, samples may be "aged" or "dried" for hours (e.g. 1-24 or more hours), days (e.g. 1-7 or more days), weeks (e.g. 1-5 or more weeks), months (e.g. 1-12 or more months), or years (e.g. 1-10 or more years). The methods of the present disclosure may also be used to distinguish samples of different ages, e.g. between two or more samples deposited at the same location or scene at different times.

In addition to characterizing cells from an unknown contributor(s), embodiments of the disclosure provide methods for training a computer for such analysis. A database or library of cell fluorescence and morphological signatures may be created using cell samples having known characteristics. According to an exemplary embodiment, an imaging flow cytometer is used to obtain microscopic images of individual cells taken at multiple fluorescent wavelengths as well as standard brightfield illumination. A series of measurements are then made on individual cells, e.g., area, length, aspect ratio, fluorescence intensity, etc. using a suitable software platform. Such platforms include, for example, commercial software (e.g., IDEAS® analysis software) and open source scripts (e.g., 'Cell Profiler' platform). Machine learning algorithms may then be applied to correlate those measurements with the known cell characteristics, such as the cell type (e.g. saliva, vaginal, blood, epidermal), and to develop a predictive framework for identifying cell characteristics in a blinded/unknown forensic sample.

In some embodiments variables may be explicitly excluded, e.g. by user selection input. As an alternative to outright exclusion, some variables may be included for analysis but attributed a weight of zero or near nero (e.g., e.g., −0.01 to 0.01, −0.001 to 0.001, 0). Variables which may be collected from cell images yet excluded from analysis for purposes of cell type classification. The reason for exclusion of a given variable may be because the variable varies with factors that are not intrinsic to the cells. For example a variable called 'raw fluorescence intensity' may be collected but is affected by fluctuations in the intensity of the laser and fluorescence of non-biological particles that may be present in the solution (i.e., not cellular).

The precise number of variables which may be employed may differ some among embodiments. Different types of geometric or fluorescence measurements (area, aspect ratio, fluorescence intensity, etc.) may each be measured at different wavelengths (e.g., six different wavelengths). Accordingly, an "area measurement," for example, may actually refer to six different measurements (Area at the first wavelength, area in the second wavelength, etc.). The same is true of other cell characteristics. Though some embodiments may employ as few as 10 or 20 variables, some exemplary embodiments use between 50 and 100, or 100 to 200, or more than 200 variables. A single "variable" may be for a specific characteristic of a cell regardless of the measuring technique or it may be a specific characteristic associated with a particular measuring technique. For instance, an exemplary embodiment may use ~150-180 variables representing 30 measurements in up to 6 fluorescent wavelengths each.

Figure 8:
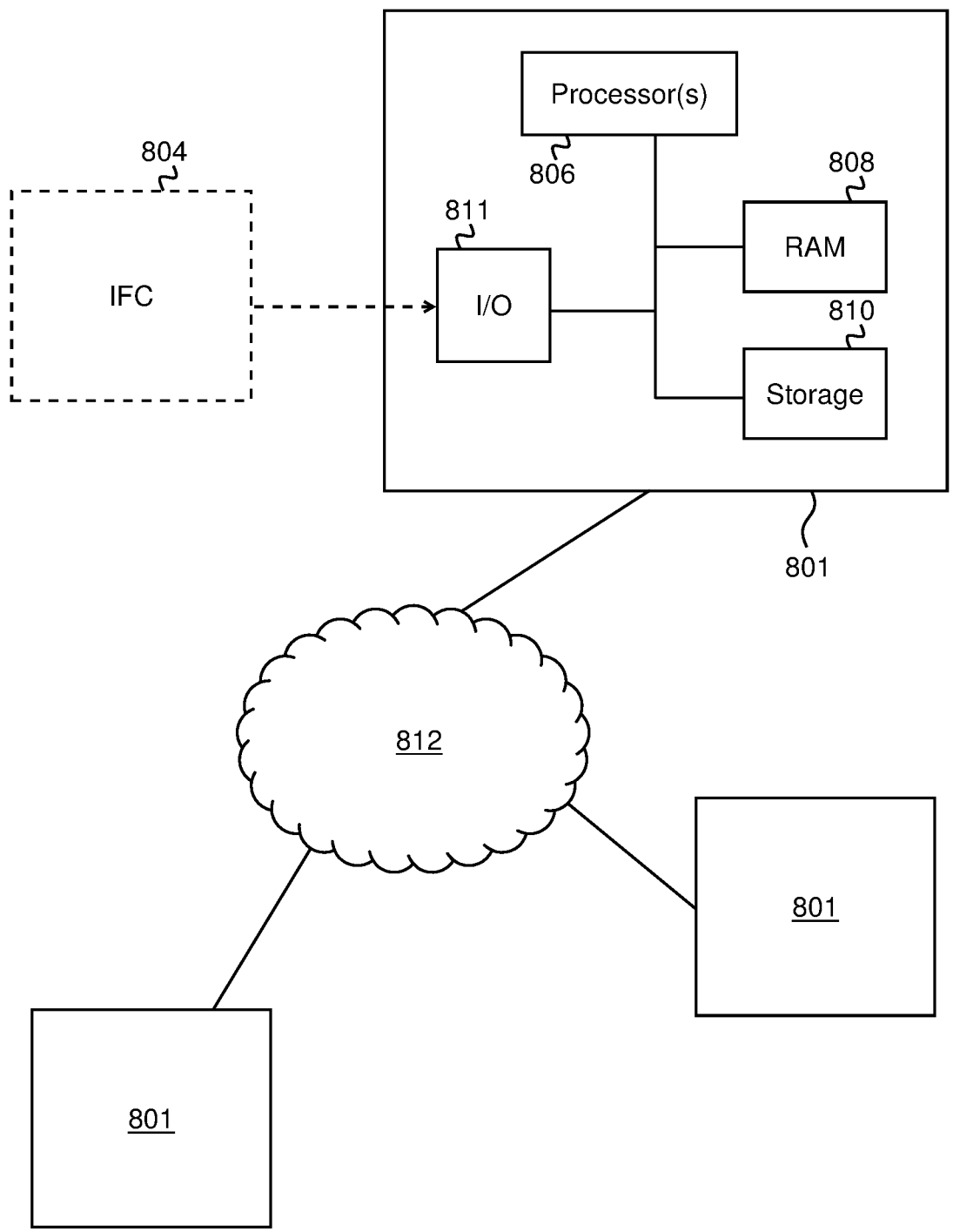
FIG. 8. An exemplary device and system according to some embodiments.

FIG. 8 is a block diagram of an exemplary device 801 or system 802 for carrying out embodiments, e.g., methods and processes discussed above. Generally a device 801 may be a computer or multiple computers. A device 801 may generally comprise one processor 806 (or multiple processors), transitory memory 808, non-transitory memory 810, and input/output device or devices 811. Other elements may also be included (e.g., power system elements) but are not illustrated. Algorithms and processes of embodiments such as described herein may be generated and/or stored with a device 801 (e.g., generated with a processor 806, stored with storage 810). The device 801 may itself be an IFC, for example, or may have data (e.g., image data) supplied to it by an IFC (e.g., by a wired connection, wireless connection, and/or over a network). A system 802 may employ multiple devices 801 why may send, receive, and/or exchange data over a network 812 or by some other means known in the art.

The stored values or ranges of values for various cell characteristics may be on a database (e.g., a non-transient computer readable medium 810) that is on or accessible to a single computer or may be stored separately on different computers within a network. In one embodiment, cells from a forensic sample are imaged using the imaging flow cytometer and measurements taken from the images are compared to stored values or ranges of values associated with certain cell characteristics. Matches from this comparison are output to the user, preferably on an automated basis. The testing may take place on the order of seconds to minutes (depending on the number of measurements desired), and the determinations, comparisons and output may take place on the order of seconds to minutes depending on the number of values to be computed and compared and the number of different stored values or value ranges to be considered.

To test a trained computer's ability to accurately assess the proportion of cell types in a sample having more than one cell contributor, simulated mixtures may be created by randomly sampling two or more donors' cell images. These images may then be classified into cell types using the remaining contributor cell populations as the reference dataset for discriminant function analysis (DFA). No human interpretation is necessary to reach the final cell classification.

The exemplary systems and methods described herein may be used by any forensic caseworking agency that processes biological evidence, e.g. for DNA profiling. This includes federal agencies, forensic service/consulting firms or laboratories, and state and local crime laboratories.

It will be readily apparent to one of ordinary skill in the art that the various processes described herein may be implemented by, e.g., appropriately programmed general purpose computers, special purpose computers and computing devices. Typically a processor (e.g., one or more microprocessors, one or more microcontrollers, one or more digital signal processors) will receive instructions (e.g., from a memory or like device), and execute those instructions, thereby performing one or more processes defined by those instructions. Instructions may be embodied in, e.g., one or more computer programs, one or more scripts.

Within this application, the term "processor" or "computer" means one or more microprocessors, central processing units (CPUs), computing devices (e.g. desk top computer, lap top computers, tablets, personal data assistants, smart phones, dongles, etc.), microcontrollers, digital signal processors, or like devices or any combination thereof, regardless of the architecture (e.g., chip-level multiprocessing/multi-core, RISC, CISC, Microprocessor without Interlocked Pipeline Stages, pipelining configuration, simultaneous multithreading). The system and method of this invention may be implemented on a single computer, a network of computers, or by cloud computing across one or multiple networks whereby the systems and networks can deliver the software which implements the system and method as a service.

Similarly, a description of a process is likewise a description of an apparatus for performing the process. The apparatus that performs the process can include, e.g., a processor and those input devices and output devices that are appropriate to perform the process. Programs that implement such methods (as well as other types of data) may be stored and transmitted using a variety of media (e.g., computer readable media) in a number of manners. In some embodiments, hard-wired circuitry or custom hardware may be used in place of, or in combination with, some or all of the software instructions that can implement the processes of various embodiments. Thus, various combinations of hardware and software may be used instead of software only.

The term "computer-readable medium" refers to any medium, a plurality of the same, or a combination of different media that participate in providing data (e.g., instructions, data structures) which may be read by a computer, a processor or a like device. Such a medium may take many forms, including but not limited to, non-volatile media, volatile media, and transmission media. Non-volatile media include, for example, optical or magnetic disks and other persistent memory. Volatile media include dynamic random access memory (DRAM), which typically constitutes the main memory. Transmission media include coaxial cables, copper wire and fiber optics, including the wires that comprise a system bus coupled to the processor. Transmission media may include or convey acoustic waves, light waves and electromagnetic emissions, such as those generated during radio frequency (RF) and infrared (IR) data communications. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH-EEPROM, any other memory chip or cartridge, a carrier wave as described hereinafter, or any other non-transient computer readable medium from which a computer can read. Various forms of computer readable media may be involved in carrying data (e.g. sequences of instructions) to a processor. For example, data may be (i) delivered from RAM to a processor; (ii) carried over a wireless transmission medium; (iii) formatted and/or transmitted according to numerous formats, standards or protocols, such as Ethernet (or IEEE 802.3), SAP, ATP, Bluetooth, and TCP/IP, TDMA, CDMA, and 3G/4G/LTE; and/or (iv) encrypted to ensure privacy or prevent fraud in any of a variety of ways well known in the art.

Output from the automated system and method may be provided to an output device which can take any form suitable for its intended purpose, and be provided to a printer, a display, a computer or network of computers, and may provide visual or audible signals which can be discerned by a user. For example, the computer(s) or network of computers used for processing information from the imaging flow cytometer may be directly or remotely connected to the imaging flow cytometer and may be in communication (wireless or wired) over a network such as the Internet.

It is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the hundredth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Example. Rapid Differentiation of Epithelial Cell Types in Aged Biological Samples Using Autofluorescent and Morphological Signatures Abstract Establishing the tissue source of cells within a biological sample is an important capability for forensic laboratories. In this study, Imaging Flow Cytometry (IFC) was used to analyze individual cells recovered from buccal, epidermal, and vaginal samples that had been dried between 24 hours and more than eight weeks. Measurements capturing the size, shape, and fluorescent properties of cells were collected in an automated manner and then used to build a multivariate statistical framework for differentiating cells based on tissue type. Results showed that epidermal cells could be distinguished from vaginal and buccal cells using a discriminant function analysis of IFC measurements with an average classification accuracy of ~94%. Ultimately, cellular measurements such as these, which can be obtained non-destructively, will provide probative information for many types of biological samples and complement results from standard genetic profiling techniques.

Methods

Sample collection and preparation. Buccal and epidermal samples were obtained from male and female volunteers pursuant to the Virginia Commonwealth University Institutional Review Board (VCU-IRB) approved protocol ID #HM20000454_CR3. Written informed consent was obtained from all participants for this study. For buccal samples, ten volunteers were asked to swab the inside of cheek for 30 seconds. Swabs were left to dry for between 24 hours and 6 days. Dried and fresh swabs were processed in the same manner. For epidermal samples, ten individuals (six of whom were buccal cell donors) were asked to hold/rub a conical tube (P/N 229421; Celltreat Scientific; Pepperell, Mass.) for five minutes to deposit cells. Tubes were then left out for 24 hours to 5 days to dry before collecting cells. Cells were collected from the surface with one sterile, pre-wetted swab, and one sterile, dry swab.

Vaginal cell samples were obtained from an existing sample repository at Virginia Commonwealth University. Samples were collected pursuant to VCU-IRB approved protocol ID #HM20002931_Ame2. Volunteers were asked to swab the inside of the vaginal cavity, and swabs were dried and stored at room temperature until analysis. Storage times ranged from 72 hours to approximately eight weeks.

All collection swabs were eluted in 1 mL of 1× Cell Staining Buffer (P/N 420201; Biolegend; San Diego, Calif.), and gently vortexed for 10 seconds. Samples were centrifuged at 1500×g at 4° C. for 5 minutes. The supernatant was discarded, and the cell pellets were dissolved in 100 uL of 1× Cell Staining Buffer for imaging flow cytometry. A list of all donor samples used in this study and their respective drying times are provided in Table 1. The IRB approved protocols required the donors to confirm that they were over 18 years of age, but did not require that their age be recorded.

TABLE 1

Tissue type and drying time for each sample.

| Buccal | | Contact Epidermal | | Vaginal | |
|---|---|---|---|---|---|
| Sample # | Time Dried | Sample # | Time Dried | Sample # | Time Dried |
| I66 | 24 hrs | L49 | 24 hrs | 1031 | 72 hrs |
| L49 | 24 hrs | N08 | 24 hrs | 2368 | 5 days |
| R47 | 48 hrs | S95 | 24 hrs | 4017 | 6 days |
| 5034 | 48 hrs | I66 | 72 hrs | 1022 | 7 days |
| C58 | 72 hrs | K36 | 4 days | 1028 | 7 days |
| 5001 | 4 days | P22 | 4 days | 4502 | 12 days |
| Y60 | 5 days | R47 | 4 days | 4504 | 12 days |
| Z32 | 5 days | Y60 | 5 days | 5021 | 14 days |
| N08 | 6 days | Z32 | 5 days | 5020 | 16 days |
| B21 | 6 days | Q17 | 5 days | 5005 | 8 weeks |

Imaging Flow Cytometry and statistical analysis. All samples were analyzed using an Amnis® Imagestream X Mark II imaging flow cytometer (EMD Millipore; Burlington, Mass.) equipped with 405 nm, 488 nm, 561 nm, and 642 nm lasers. Laser voltages for all tests were set at 120 mW, 100 mW, 100 mW and 150 mW, respectively. Images of individual events were captured in five detector channels labeled: 1 (430-505 nm), 2 (505-560 nm), 3 (560-595 nm), 5 (640-745 nm), and 6 (745-780 nm). Channel 4 was used to capture Brightfield images. Magnification was set at 40× and autofocus was enabled so that the focus varied with cell size. Aspect ratio and area values for samples of each cell type are comparable to forward scatter/side scatter measurements collected with conventional flow cytometry instrumentation. Raw image files (.rif) were then imported into IDEAS® design software (EMD Millipore; Burlington, Mass.). Display Width and Display Height were changed to 120×120 pixels for each image. The 'Shape Change Wizard' option in the software was used to select focused cells on a Gradient RMS_M04Ch04×Normalized Frequency histogram. Once the data was filtered for focused cells, single cells were selected on an Area_M04×Aspect Ratio_M04 scatterplot. This was to ensure that cell aggregates were not incorporated into the downstream analysis.

Data for individual cell events were collected for 17 different features: area, aspect ratio, aspect ratio intensity, contrast, intensity, mean pixel, median pixel, max pixel, length, width, height, brightness detail intensity ('R3' pixel increment), raw centroid X, raw centroid Y, and circularity. These feature measurements were collected across multiple detector channels (i.e., fluorescence and brightfield wavelengths) with the exception of measurements that could only be determined from brightfield images such as centroid X/Y and circularity. This yielded a total of 88 measurements/variables collected for each cell. Cell yield varied across each of the study samples but did not appear to be correlated with tissue type, drying time, or individual donor. Most cell populations yielded between 200 and 400 cell images with nine samples providing between 80 and 200 images.

IFC measurement values were then imported into SPSS® v23 statistical software (IBM, Inc. Chicago, Ill.). Differences in mean values between the three cell types were tested using a one-way ANOVA analysis with a Tukey HSD post-hoc test. Next, multivariate differences among the three cell type groups were analyzed using a Discriminant Function Analysis (DFA) based on the within-group covariance matrix. Results were initially compared from direct analysis of IFC measurements and those obtained from transforming the data first into principal components (PCs) and then conducting DFA on the PC scores. It was found that the latter approach led to less differentiation in the canonical variate plot and poorer classification accuracy and thus direct analysis of raw measurements was used. Initially all data from all collected variables were tested for cell type differentiation. Small sets of variables (<5) were then systematically excluded to investigate whether group separation in the canonical variate plot and classification accuracy improved. This was done iteratively until a final set/combination of variables (88 total) was identified that resulted in the greatest degree of separation in the canonical variate plot and the highest rate of accurate classifications.

Results

It was first determined whether IFC could be used to distinguish cells from the three different epithelial tissue sources. During image collection and processing, some general qualitative differences between images from each of the three cell types were noted. For example, circular features with a size consistent with nuclei (~8 μm), were observed in the center of many of the buccal cells and vaginal cells (e.g., Images 1507, 1796, respectively, FIG. 2), while they were rarely observed in epidermal cell images. The presence of nuclei could be used to confirm the presence of buccal or vaginal cells but is not a required aspect of exemplary embodiments disclosed herein. Buccal and vaginal cells were generally larger in size, >40 μm compared to epidermal cells, which were ~20-50 μm although some size overlap between cell sources was noted. This could be due in part from the folding or degradation of buccal and vaginal cells during drying or sampling prior to IFC. Epidermal cells generally exhibited higher contrast features in brightfield images compared to buccal or vaginal cells.

For the 264 pairwise comparisons between group means (88 variables and three sample groups), only 42 yielded p-values greater than 0.01, with the vast majority showing p values less than 0.0001. Of note were differences in means for circularity (7.8 epidermal, 4.1 buccal, 4.3 vaginal), intensity (e.g., in 430-505 nm channel $3\times10^5$ RFU epidermal, $6\times10^4$ RFU buccal, $5\times10^4$ RFU vaginal), and brightness detail (e.g., in 403-505 nm channel $1\times10^4$ RFU epidermal, $9\times10^3$ buccal, $7\times10^3$ RFU vaginal). However, the range of values for each cell group showed a high degree of overlap across the three cell types. Similarly, most variables showed large standard deviations for each cell type, with coefficients of variation for individual measurements ranging from ~20% to more than 280%.

In order to determine whether the observed variation in IFC measurements could be used to differentiate cell types, Discriminant Function Analysis (DFA) was employed as a supervised multivariate technique to model variation between groups. In DFA, linear combinations of the original variables are constructed (i.e., canonical variates) such that the variation between user-defined sample groups is maximized and within group variation is minimized. DFA is a well-established technique with demonstrated applications for other forensic signature systems [10-12]. For this dataset, the primary advantages of DFA are that differences in measurement scales across variables do not impact the analysis and it is relatively robust to non-normally distributed data [13]. Additionally, the canonical variates generated with DFA can be used to classify individual samples into one of the user-defined groups. For this study, DFA was used to initially examine multivariate differences between groups. A DFA plot of all IFC measurements from the three cell types showed distinct separation between buccal, epidermal, and vaginal cell populations (FIG. 3). Multivariate differences between groups were statistically significant, Wilk's Lambda=0.114, p<0.001. Some overlap is observed among the sample groups on the DFA plot, in particular between buccal and vaginal cell groups. A leave-one-out (LOO) classification on individual cell images for each of the three groups and all 30 cell populations showed an overall classification accuracy of ~90%.

Next algorithms constructed based on a discriminant function analysis framework were used to classify entire donor cell populations into one of the three cell groups in a blinded fashion to determine the accuracy and robustness of this approach for identifying cell types from an unknown forensic sample. This was accomplished by withholding a given donor cell population from the DFA and classifying each cell image into one of the three epithelial cell types based on information from the remaining contributor cell populations. In general, epidermal cells showed the highest overall classification accuracy (88%) with six of the ten donor cell populations having accuracies over 90%. Only one cell population, P22, was below 80%. Buccal and vaginal cell populations yielded lower overall classification rates, 72% and 75% respectively. Interestingly, classification accuracies were highly variable across individual cell populations for these two groups, with buccal cells ranging between 24% and 96% and vaginal cells ranging between 26% and 95%.

In an attempt to improve the classification accuracy for each cell type, individual cell populations were also tested with two-group classification schemes where one tissue group was excluded completely from the analysis, i.e., buccal cells against epidermal cells; vaginal cells against epidermal cells; and buccal cells against vaginal cells. Simplified classification schemes could be run subsequent to the original classification to help identify samples assigned to one of the closely related sample groups, i.e., a cell image classified as a buccal cell in the three group DFA could then be run against a two group DFA containing only buccal and vaginal cells. Additionally, two group comparisons could approximate caseworking scenarios in which one of the epithelial cell types could be ruled out a fortiori for an unknown cell population. Results from two-group DFA generally showed improved classification accuracy. Buccal and epidermal cell populations could be differentiated with the highest accuracy (~94%). The lowest classification rate of individual donor cell populations in this comparison was 80% (P22, Epidermal) with the majority of cell populations exhibiting classification accuracy of 95% or higher. The vaginal-epidermal cell classifications showed comparable results with an overall classification accuracy of ~91%. Two individual cell populations in this scheme exhibited markedly lower success rates (P22 epidermal 63% and 5005 vaginal 32%). However, the remaining cell populations had classification accuracy>80% with the majority>95%. Less differentiation was observed between buccal and vaginal cells with an overall classification accuracy of 78%. Seven donor cell populations still showed accuracies greater than 95% and three donor cell populations were below 60% accuracy (e.g., 5034, Buccal; 2368 Vaginal; 1028 Vaginal).

To investigate whether the DFA classification scheme can accurately assess the proportion of cell types in a two-person mixture, simulated mixtures were created by randomly sampling two donors' cell images. These images were then classified into cell types using the remaining contributor cell populations as the reference dataset for DFA. A 1:1 simulated mixture consisting of L49 (epidermal) and B21 (buccal) cell images was classified as 50% epidermal cells and 46% buccal cells, with the remaining 4% of images classifying as vaginal cells. Using the two-group classification scheme, the cell population was determined to be 50% epidermal cells and 50% buccal cells. Similar results were obtained for a 1:1 simulated mixture consisting of Q17 (epidermal) and 1031 (vaginal) cell images, with the population characterized as 49% epidermal cells, 49% vaginal cells and 2% buccal cells. The two group classification scheme estimated a cell population of 50% epidermal cells and 50% vaginal cells. Mixtures containing contributor populations that demonstrated lower classification accuracy in earlier experiments had lower success rates. For example, a 1:1 simulated mixture consisting of C58 (buccal) and R47 (epidermal) cell images classified as 42% epidermal cells, 51% buccal cells, and 7% vaginal cells.

Discussion

Overall, the relatively high classification accuracy of epidermal cells against buccal cells and epidermal cells against vaginal cells (>90%) suggests that systematic differences in morphological and/or optical properties measured by IFC can be used to distinguish between epithelial cell types in these comparison schemes (i.e., IFC using all 88 variables with different weights). Further, measurement values can be used to construct an analysis framework for characterizing unknown cell populations into one of these three sample groups. The observed variation between sloughed epidermal cells and buccal/vaginal cells is consistent with the intrinsic biochemical, structural, and morphological differences for cells originating from each tissue source. For example, shed epidermal cells are derived from the stratum corneum and characterized by a high degree of keratinization with few if any organelles and little intracellular DNA owing to the apoptotic processes occurring as cells migrate from the basal to the upper layers of the epidermis [15]. In contrast, buccal and vaginal cells are derived from less stratified epithelial tissue and may be only partially keratinized or unkeratinized. Although no studies to date have explicitly surveyed cellular differences between these three tissue sources using fluorescence signatures, previous work has shown that changes in cellular autofluorescence can be used to differentiate layers of epidermal tissue with different intracellular components (e.g., keratin, tryptophan, FAD) [16,17]. Additionally, the morphological and size differences detected with IFC (e.g., area and circularity measurements) are consistent with histological context of each cell type, i.e., shed epidermal cells hexagonal and ~20-50 µm, while buccal and vaginal cells are typically >40 µm with elongated shapes [18,19].

Figure 4B:
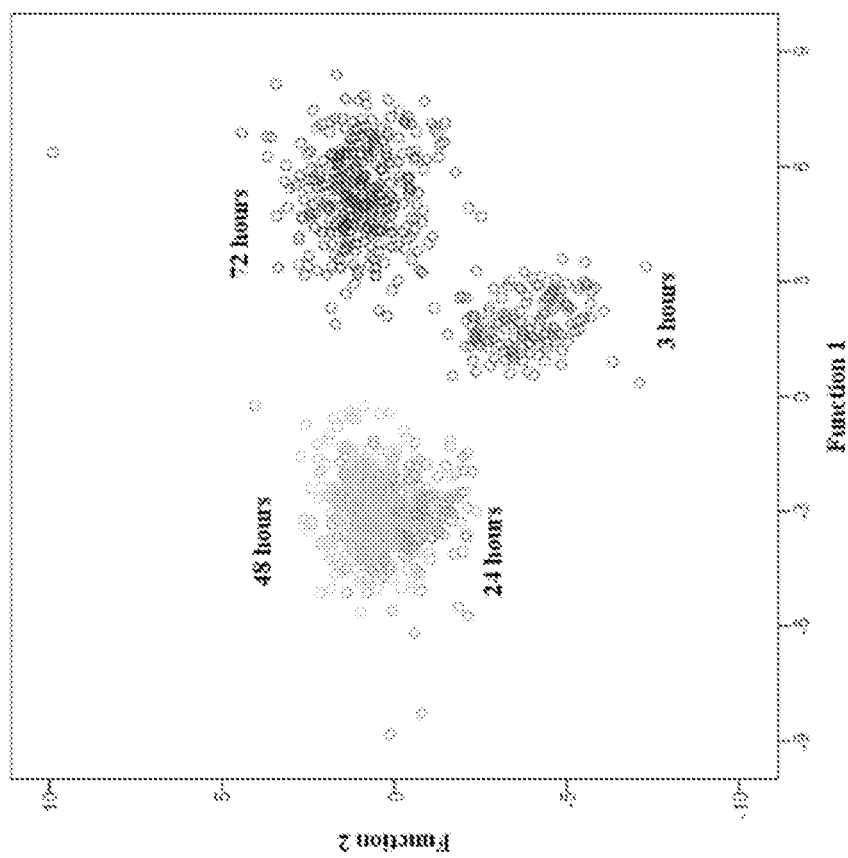
FIGS. 4A and 4B. DFA of buccal cell populations from the same donor (A: I66 and B: L49) aged for different amounts of time.
Figure 4A:
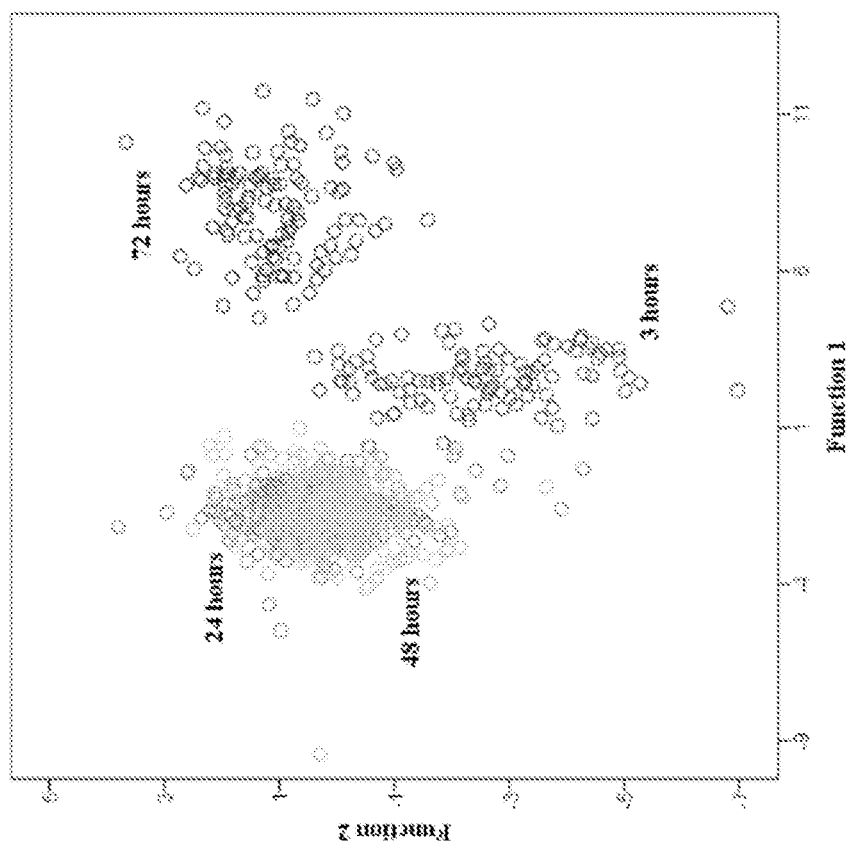

The overlap between cell sources shown in FIG. 3 and misclassifications of individual cell images may be impacted by a number of factors. First, some similarities in fluorescence and/or morphological attributes are expected, particularly for buccal and vaginal cells given that both are derived from non-keratinized epithelial tissue. This is consistent with poorer classification accuracy of buccal-vaginal cell comparisons relative to buccal-epidermal and vaginal-epidermal. Second, cell populations in this data set represent a wide range of drying/exposure times prior to sampling and analysis. Levels of intrinsic fluorescence are likely to change with time owing to the degradation of cellular components such that specimens with longer periods of environmental exposure may be harder to distinguish from each other. There were no clear relationships between exposure time and misclassification rate or position on the DFA plot (FIG. 3). An analysis of buccal cell populations from two donors, each aged for 3, 24, 48, and 72 hours, suggests that fluorescence and/or morphological features may change in a characteristic way over time (FIG. 4A-B). For example, the average intensity of autofluorescence for buccal cells and blood cells increases over a certain period of time between 1 day and 7 days. Then after 2 weeks, there is not a clear trend in autofluorescence over time but there is some indication that it may undergo some change.

Figures 5A, 5B:
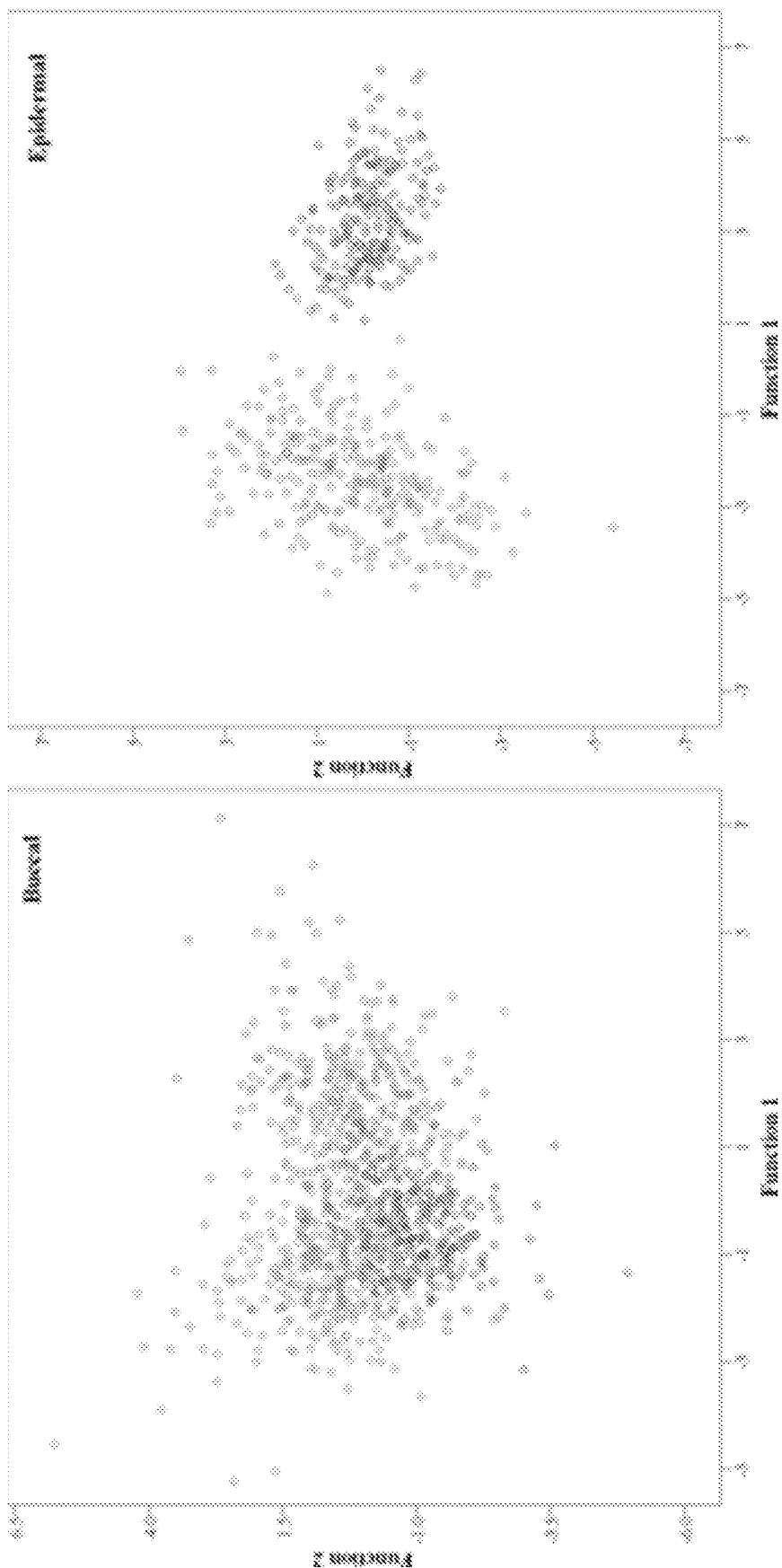
FIGS. 5A and 5B. DFA of cell populations derived from three different contributors for buccal (A) and epidermal (B) tissue sources. Buccal cells were dried for 48 hours at room temperature and epidermal cell samples were dried for 24 hours at room temperature prior to analysis.

Another factor that could be contributing to misclassifications is inter-individual variation. Previous work has shown that autofluorescence signatures in shed epidermal cells can vary between contributors, likely owing to the presence of exogenous materials associated with the cell [20]. Cell populations from different contributors of the same tissue type (epidermal or buccal) and drying time (24 or 48 hours, respectively) showed some separation in a DFA (FIG. 5A-B). Increasing the number of unique donor cell populations in the reference/comparison dataset may increase the isolation of any tissue-specific signatures that are present. Nevertheless, contributor-specific variation in IFC measurements may be used for estimating the number of individual cell populations in a biological sample and/or facilitating front-end cell separation in a DNA profiling workflow.

It should also be noted that earlier studies have suggested that sex-specific differences in the size and morphology of epidermal cells may exist [18]. Although there were no obvious differences in classification accuracy or position on the DFA plot across male and female donors, IFC could be a viable approach for systematically testing for sex specific signatures in a larger dataset of epidermal cell populations.

The goal of this study was to conduct an assessment of high-throughput analysis of autofluorescence and morphological signatures and its applications for characterizing epithelial cell types in an unknown biological sample. An important aspect of this workflow is that intrinsic properties of the cell are being analyzed and no biochemical or immunological stains or probes are required. High-throughput, single cell measurements combined with a multivariate classification framework were used to distinguish epidermal cells from other epithelial cell sources across a range of drying times with an overall high degree of accuracy. Although a range of factors may contribute to morphological or optical properties in any given sample (e.g., individual-specific signatures and degradation time), these results suggest that multivariate approaches may be used to extract tissue-specific signatures from biological samples.

REFERENCES

1. Haas C, Klesser B, Kratzer A, Bär W (2008) mRNA profiling for body fluid identification.
   Forensic Science International: Genetics Supplement Series 1: 37-38.
2. Seashols-Williams S, Lewis C, Calloway C, Peace N, Harrison A, et al. (2016) High-throughput miRNA sequencing and identification of biomarkers for forensically relevant biological fluids. Electrophoresis 37: 2780-2788. pmid:27557737
3. Silva S S, Lopes C, Teixeira A L, Carneiro de Sousa M J, Medeiros R (2015) Forensic miRNA: potential biomarker for body fluids? Forensic Sci Int Genet 14: 1-10. pmid:25280377

4. Legg K M, Powell R, Reisdorph N, Reisdorph R, Danielson P B (2017) Verification of protein biomarker specificity for the identification of biological stains by quadrupole time-of-flight mass spectrometry. Electrophoresis 38: 833-845. pmid:27943336
5. Forat S, Huettel B, Reinhardt R, Fimmers R, Haidl G, et al. (2016) Methylation Markers for the Identification of Body Fluids and Tissues from Forensic Trace Evidence. PLoS ONE 11: e0147973. pmid:26829227
6. Verdon T J, Mitchell R J, Chen W, Xiao K, van Oorschot R A (2015) FACS separation of non-compromised forensically relevant biological mixtures. Forensic Sci Int Genet 14: 194-200. pmid:25450793
7. Dean L, Kwon Y J, Philpott M K, Stanciu C E, Seashols-Williams S J, et al. (2015) Separation of uncompromised whole blood mixtures for single source STR profiling using fluorescently-labeled human leukocyte antigen (HLA) probes and fluorescence activated cell sorting (FACS). Forensic Sci Int Genet 17: 8-16. pmid:25796046
8. Han Y, Gu Y, Zhang A C, Lo Y H (2016) Review: imaging technologies for flow cytometry. Lab Chip 16: 4639-4647. pmid:27830849
9. Taki T, Kibayashi K (2015) Characterization of cellular and extracellular DNA in saliva. Leg Med (Tokyo) 17: 471-474. pmid:26593992
10. Johnson D R, O'Higgins P, Moore W J, McAndrew T J (1989) Determination of race and sex of the human skull by discriminant function analysis of linear and angular dimensions. Forensic Sci Int 41: 41-53. pmid:2636546
11. Ehrhardt C J, Chu V, Brown T, Simmons T L, Swan B K, et al. (2010) Use of fatty acid methyl ester profiles for discrimination of *Bacillus cereus* T-strain spores grown on different media. Appl Environ Microbiol 76: 1902-1912. pmid:20097814
12. Hanssen E N, Avershina E, Rudi K, Gill P, Snipen L (2017) Body fluid prediction from microbial patterns for forensic application. Forensic Sci Int Genet 30: 10-17. pmid:28605650
13. Huberty C J. Applied Discriminant Analysis. 1st ed. New York: John Wiley & Sons, Inc; 1994.
14. Ehrhardt C J, Murphy D L, Robertson J M, Bannan J D (2015) Fatty Acid Profiles for Differentiating Growth Medium Formulations Used to Culture *Bacillus cereus* T-strain Spores. J Forensic Sci 60: 1022-1029. pmid:25854710
15. Lippens S, Denecker G, Ovaere P, Vandenabeele P, Declercq W (2005) Death penalty for keratinocytes: apoptosis versus cornification. Cell Death Differ 12 Suppl 2: 1497-1508. pmid:16247497
16. Fereidouni F, Bader A N, Colonna A, Gerritsen H C (2014) Phasor analysis of multiphoton spectral images distinguishes autofluorescence components of in vivo human skin. J Biophotonics 7: 589-596. pmid:23576407
17. Zeng H, MacAulay C, McLean D I, Palcic B (1995) Spectroscopic and microscopic characteristics of human skin autofluorescence emission. Photochem Photobiol 61: 639-645. pmid:7568410
18. Plewig G (1970) Regional differences of cell sizes in the human stratum corneum. II. Effects of sex and age. J Invest Dermatol 54: 19-23. pmid:5416674
19. Paszkiewicz G M, Timm E A, Mahoney M C, Wallace P K, Sullivan Nasca M A, et al. (2008) Increased human buccal cell autofluorescence is a candidate biomarker of tobacco smoking. Cancer Epidemiol Biomarkers Prev 17: 239-244. pmid:18199730
20. Katherine Philpott M, Stanciu C E, Kwon Y J, Bustamante E E, Greenspoon S A, et al. (2017) Analysis of cellular autofluorescence in touch samples by flow cytometry: implications for front end separation of trace mixture evidence. Anal Bioanal Chem 409: 4167-4179. pmid:28516277
21. Jones T R, Kang I H, Wheeler D B, Lindquist R A, Papallo A, et al. (2008) CellProfiler Analyst: data exploration and analysis software for complex image-based screens. BMC Bioinformatics 9: 482. pmid:19014601

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

What is claimed is:

1. A method of characterizing cells from an unknown contributor or contributors in a forensic sample, comprising
    obtaining a plurality of morphological and autofluorescence measurements from a plurality of cells in the forensic sample;
    classifying the plurality of cells into a plurality of groups using two or more classifications, each classification comprising
        calculating at least two coordinate values for each cell using respective first and second functions that are weighted combinations of the plurality of morphological and/or autofluorescence measurements, and
        sorting each cell into one of the plurality of groups based on ratios of multivariate distances between the calculated coordinate values and multivariate centroids of cell groups in a reference dataset; and
    outputting information for the plurality of groups based on the classifying step.

2. The method of claim 1, wherein the two or more classifications are performed successively, wherein for any two classifications in immediate succession, only the cells sorted into the second group by the first classification are subjected to the second classification.

3. The method of claim 2, wherein the respective functions of the two or more classifications contain the same plurality of morphological and autofluorescence variables but different weightings.

4. The method of claim 1, further comprising using the output information for downstream DNA profiling and/or crime reconstruction.

5. The method of claim 1, wherein the plurality of groups are all epithelial cell types.

6. The method of claim 5, wherein the plurality of groups comprise epidermal, buccal, and vaginal.

7. The method of claim 6, wherein the two or more classifications include a first binary classification that differentiates epidermal cells from non-epidermal cells and a second binary classification that differentiates buccal cells from vaginal cells, wherein the second binary classification is performed only for cells classified by the first binary classification as non-epidermal cells.

8. The method of claim 1, further comprising counting a total cell count for each group of the plurality of groups after all classifications are complete.

9. The method of claim 1, wherein the step of obtaining comprises generating images of individual cells and analyzing the images to obtain the plurality of morphological and autofluorescence measurements without biochemical or immunological stains or probes.

10. The method of claim 9, wherein the measurements are obtained with an imaging flow cytometer.

11. The method of claim 1, wherein the one or more morphological and/or autofluorescence measurements are selected from the group consisting of area, aspect ratio, aspect ratio intensity, contrast, fluorescence intensity, mean pixel, median pixel, max pixel, length, width, height, brightness detail intensity ('R3' and 'R7' pixel increments), and circularity.

12. A method of training a computer for analysis of forensic samples, comprising
obtaining for a plurality of morphological variables a plurality of measurements from a plurality of cells having one or more known characteristics; and
generating two or more functions which comprise weighted combinations of the plurality of morphological variables such that the variation between user-defined sample groups is maximized and within group variation is minimized, the two or more functions being usable or used to classify or characterize further cells from an unknown contributor.

13. The method of claim 12, wherein the measurements are obtained with an imaging flow cytometer.

14. The method of claim 12, wherein the plurality of morphological variables are selected from the group consisting of area, aspect ratio, length, width, height, and circularity.

15. The method of claim 12, wherein the one or more known characteristics comprises time since cell deposition and wherein the two or more functions are usable or used to classify or characterize further cells based on the time since cell deposition.

16. A device comprising one or more processors and a computer readable storage medium, the computer readable storage medium having instructions executable by the one or more processors for characterizing cells from an unknown contributor or contributors in a forensic sample, said instructions when executed causing the device to perform:
obtaining a plurality of morphological measurements from a plurality of cells in the forensic sample;
with the one or more processors, classifying the plurality of cells into a plurality of groups using two or more classifications, each classification comprising
calculating at least two coordinate values for each cell using respective first and second functions that are weighted combinations of the plurality of morphological measurements, and
sorting each cell into one of the plurality of groups based on ratios of multivariate distances between the calculated coordinate values and multivariate centroids of cell groups in a reference dataset; and
outputting information for the plurality of groups based on the classifying step.

17. The device of claim 16, wherein the two or more binary classifications are performed successively, wherein for any two binary classifications in immediate succession, only the cells sorted into the second group by the first binary classification are subjected to the second binary classification.

18. The device of claim 17, wherein the respective functions of the two or more binary classifications contain the same plurality of morphological variables but different weightings.

19. The device of claim 16, wherein the plurality of groups are all epithelial cell types.

20. The device of claim 19, wherein the plurality of groups comprise epidermal, buccal, and vaginal.

21. The device of claim 20, wherein the two or more classifications include a first binary classification that differentiates epidermal cells from non-epidermal cells and a second binary classification that differentiates buccal cells from vaginal cells, wherein the second binary classification is performed only for cells classified by the first binary classification as non-epidermal cells.

22. The device of claim 16, further comprising counting a total cell count for each group of the plurality of groups after all classifications are complete.

23. The device of claim 16, wherein the step of obtaining comprises generating images of individual cells and analyzing the images to obtain the plurality of morphological measurements.

24. The device of claim 23, wherein the measurements are obtained with an imaging flow cytometer.

25. The device of claim 16, wherein the one or more plurality of morphological variables are selected from the group consisting of area, aspect ratio, length, width, height, and circularity.

26. A method of characterizing cells in a forensic sample, comprising
obtaining a plurality of morphological and/or autofluorescence measurements from the cells in the forensic sample, wherein the morphological and/or autofluorescence measurements are obtainable non-destructively and without biochemical or immunological stains or probes;
classifying the plurality of cells into groups by
calculating values for the plurality of cells based on weighted combinations of the morphological and/or autofluorescence measurements,
sorting each cell into one of a plurality of groups based on a comparison of the calculated values and values in a reference dataset; and
outputting information for the plurality of groups based on the classifying step.

* * * * *